United States Patent [19]

Perrault

[11] Patent Number: 4,872,268

[45] Date of Patent: Oct. 10, 1989

[54] SKELETON DEVICE

[76] Inventor: Ronald Perrault, 3 avenue des Sapins, Notre-Dame-des-Prairies, Canada, J6E 1C3

[21] Appl. No.: 186,094

[22] Filed: Apr. 20, 1988

[51] Int. Cl.$^4$ .............................................. G01B 3/02
[52] U.S. Cl. ......................................... 33/512; 33/7; 33/391
[58] Field of Search ...................... 33/512, 511, 7, 370, 33/371, 374, 375, 381, 391, 384, 383; 128/774, 781, 68, 75

[56] References Cited

U.S. PATENT DOCUMENTS

| | | | |
|---|---|---|---|
| 809,836 | 1/1909 | Nordstrom | 33/375 |
| 1,014,402 | 1/1912 | Larsen | 33/383 |
| 1,131,596 | 3/1915 | Bowen | 33/371 |
| 1,161,504 | 11/1915 | Miller | 33/512 |
| 1,454,693 | 8/1921 | Schlattau | 33/383 |
| 1,863,236 | 6/1932 | Brienza | 33/7 |
| 2,092,179 | 10/1936 | Nosal | 33/7 |
| 2,137,583 | 11/1938 | Orvold | 33/7 |
| 4,201,226 | 5/1980 | Phillips | 33/512 |

*Primary Examiner*—William A. Cuchlinski, Jr.
*Assistant Examiner*—Christopher W. Fulton

[57] ABSTRACT

A device for three-dimensional measurements of body portions relative to overall body posture. The device includes two diverging main arms, being elongated, rigid and cylindrical, and pivotally interconnected at one end by a transverse bolt. Two elongated, rigid, cylindrical, support rods are mounted transversely to one of the main arms, one rod slidable lengthwisely thereof. Each arm includes a spirit level embedded therein, and one arm further includes a scale plate embedded therein. A transverse scale ruler is pivoted spacedly to two sleeves slidable along one and the other arm, respectively. A gravitational goniometer is mounted to the main arm not connected to the rods, for lengthwise displacement thereabout. The rods are to abut joint portions of a human body, and at least one of the spirit levels and goniometer to be levelled before the scales can be effectively used, cooperatively with comparison charts of normal dimensions-posture ratios data.

9 Claims, 3 Drawing Sheets

SKELETON DEVICE

FIELD OF THE INVENTION

This invention relates to specialized tools for use by paramedical personnel, and more specifically for use in reconstructive surgery, orthopaedics, and physiotherapy.

BACKGROUND OF THE INVENTION

Constant developments in current medical science have brought several improvements in tools used in this art. For example, tools in orthopaedics and physiotherapy have helped a great number of motor vehicle accidents victims to recover from their wounds.

In the case of a leg being sectioned during a car accident, it is now possible, through reconstructive surgery or other non-surgical techniques, to replace the leg by an artificial limb which may at least appear to be both structurally and functionally similar to the original. Such artifical limbs or parts thereof are also required in cases or persons suffering from lifelong anatomical difformities.

In such circumstances, it is hardly necessary to underline that adequate measurement of the relative proportions of the body parts in respect with the body posture, is paramount for the success thereof.

As of now, there is made use of gravitational gonimeters to measure relative disposition of limbs relative to posture; but such tool is limited to two dimensional measurement computations. There is no specialized tool available on the market, to the knowledge of the inventor, which is specifically directed to correlating normal proportions of length of limbs of a human body relative to the posture of that human body, taking into account dissymmetry of either functional or structural nature of the skeleton. Such a tool should thus be able to make three-dimensional measurement computations of relative positions of body portions.

OBJECTS OF THE INVENTION

The main object of the present invention is therefore to provide a tool that will meet the above-noted requirements.

Another object of this invention is that the tool be light in weight, so as to be easily handled by a single technician.

SUMMARY OF THE INVENTION

Accordingly with the objects of the invention, there is disclosed a skeleton-measuring device comprising one and another main arms, said arms being elongated, rigid and cylindrical. First mounting means interconnects said arms for pivotal movement of said another arm relative to said one arm about a first plane; support means supports said another arm over joint portions of a human body; level means monitors horizontal leveling of both of said arms. A scale member, connected to said one arm by second mounting means and to said another arm by third mounting means, is provided for both pivotal movement about a second plane parallel to said first plane and lengthwise displacement relative to either of said arms; and scale means measures the lengthwise displacement of the scale member relative to said another arm.

DETAILED DESCRIPTION OF THE PREFERRED EMBODIMENT OF THE INVENTION

Figure 3:
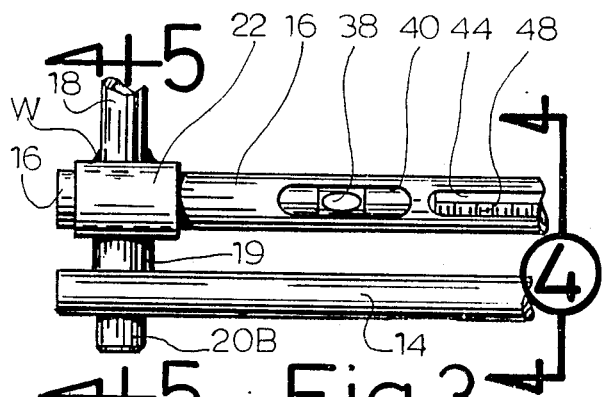
FIGS. 3, 6, and 9 are enlarged, fragmentary, plan views of level means, scale means and goniometer means respectively of FIG. 1.
Figure 4:
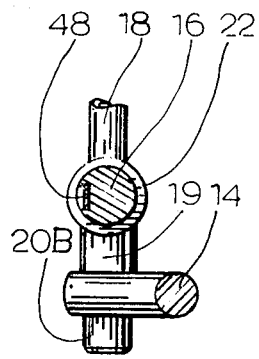
FIGS. 4 and 5 are cross-sectional views taken along lines 4—4 and 5—5, respectively, of FIG. 3.
Figure 5:
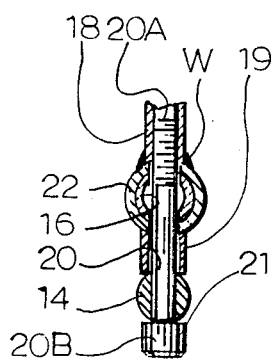

The present invention consists of a device, generally denoted 12, made of two elongated, main, cylindrical, rigid, straight arms 14, 16 pivotally interconnected on one side by a bolt 20. A spacer sleeve 19 surrounds bolt 20 in between arms 14 and 16. The threaded end 20A (FIG. 5) of bolt 20 screwingly engages within one end of a hollow cylindrical rod 18 having mating inner threads. Arm 14 is full and lengthwisely straight. Arm 16 is full, except at its portion in register with bolt 20, where it is surrounded by an enlarged sleeve 22. Sleeve 22 is fixedly secured at weld point W (FIG. 3) to rod 18. Arm 16 is lengthwisely directed progressively away from arm 14, starting from sleeve 22.

Figure 1:
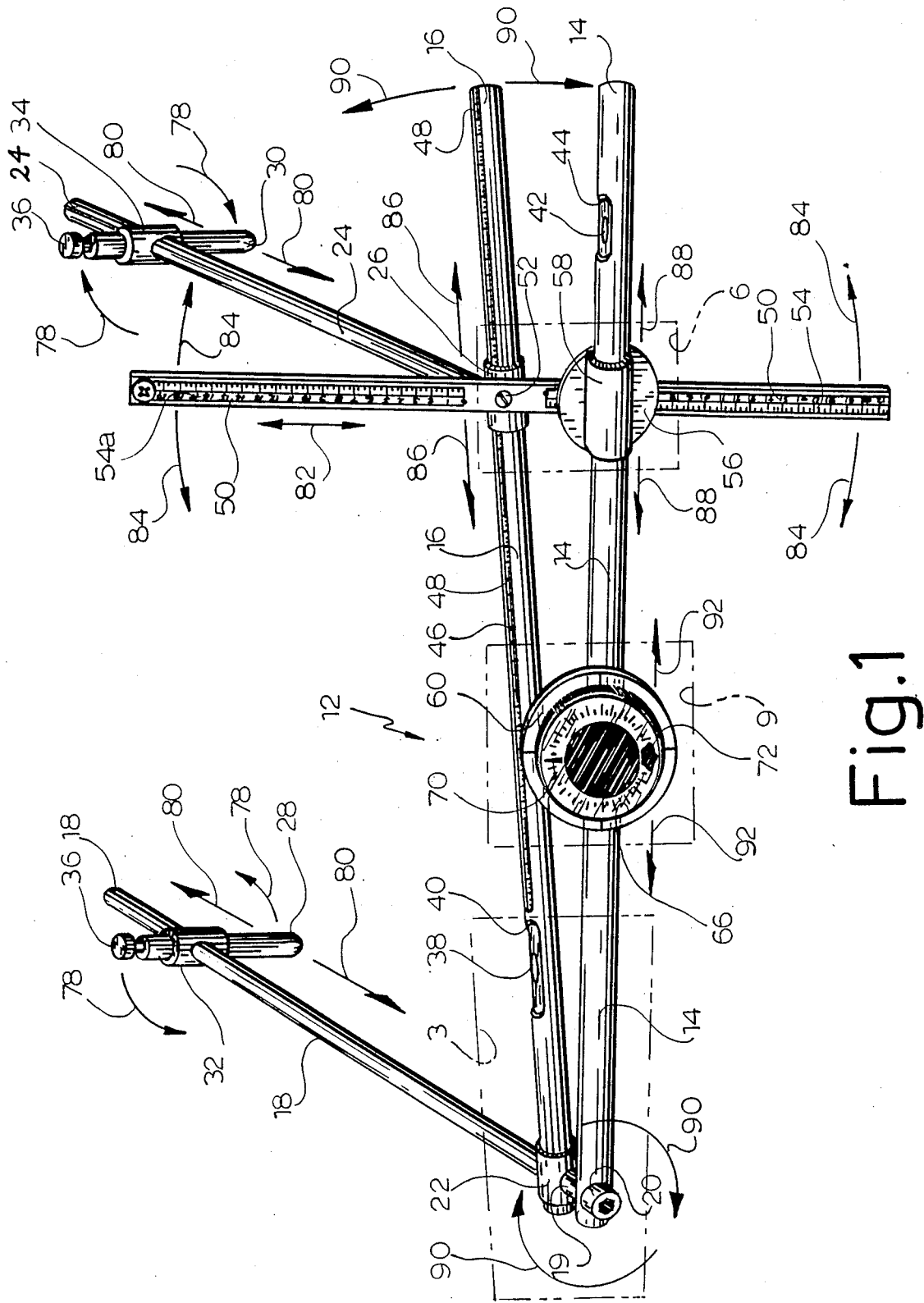
FIG. 1 is a perspective view of a measuring device according to a preferred embodiment of the invention, showing the relative play of the constituting elements thereof.
Figure 7:
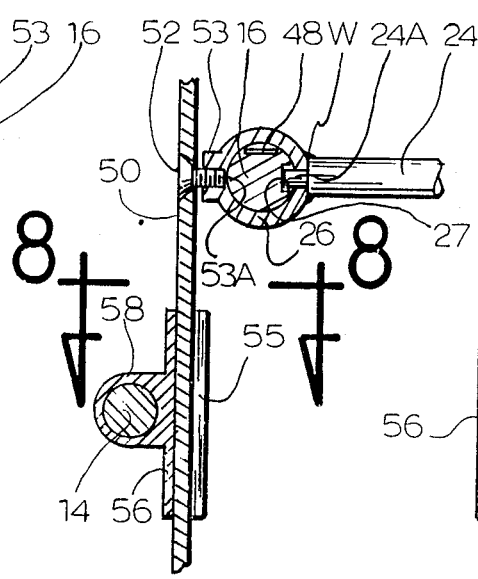
FIG. 7 is a cross-sectional view taken along line 7—7 of FIG. 6.

The enlarged head 20B of bolt 20 defines a seat 21 against which abuts arm 14, to prevent disengagement of the latter. Another transverse elongated cylindrical rod 24 is mounted at one end thereof to an enlarged sleeve 26 surrounding an intermediate portion of cylindrical arm 16. More particularly, rod 24 includes a diametrically smaller end stud 24A (FIG. 7), which engages through the wall of sleeve 26, and into a longitudinal groove 27, made in the outer surface of arm 16, for registering alignment therewith. Rod 24 is moreover fixedly secured to sleeve 26 by weld points W. Stud 24A prevents rotation of sleeve 26 on arm 16, while permitting its sliding movement on arm 16, as indicated by arrows 86 (FIG. 1).

Further short cylindrical rods 28, 30 are fixed in sleeves 32, 34, which are transversely engaged by intermediate portions of rods 18, 24, respectively, for either pivotal action or slidable movement lengthwisely relative to their corresponding support rod 18, 24. Each short rod 28, 30 may be locked in position against relative movement and relative to its support rod 18 or 24, by a set-screw 36, in the known fashion.

There is provided a spirit level 38, embedded within arm 16 and made to appear through a small window 40 made in the outer wall of arm 26, near sleeve 22. A second spirit level 42 is embedded in the body of arm 41 and appears through a small window 44 made in the outer wall of arm 14 proximate its free end. Both windows 40, 44 preferably open on the same side of their arms.

A further elongated window 46 is provided about the outer wall of arm 16 and extends from the free end thereof to slightly short the window 40. A metric graduation scale 48, embedded in arm 16, appears through window 46, which again preferably opens on the same side as windows 40, 44. Scale 48 defines a plane, preferably at right angle to that of the longitudinal groove 27 of arm 16. Graduation scale 48 is designed to measure the differential lengthwise displacement of transverse rod 24 relative to arm 16.

A second metric scale member is provided, in the shape of an elongated rectangular rigid scale ruler 50, pivotally mounted at its intermediate portion to sleeve 26 by a screw 52. Sleeve 26 further includes a small intermediate flat shoulder 53 (FIG. 7), correponding to a thickened portion of its wall, and defining a threaded bore 53A, for screwing screw 52 thereinto. Ruler 50 thus abuts against the flat face of shoulder 53. The axis of threaded bore 53A should preferably be parallel to the plane defined by scale 48 and co-axial to the axis of stud 24A engaging groove 27 of arm 26.

Figure 6:
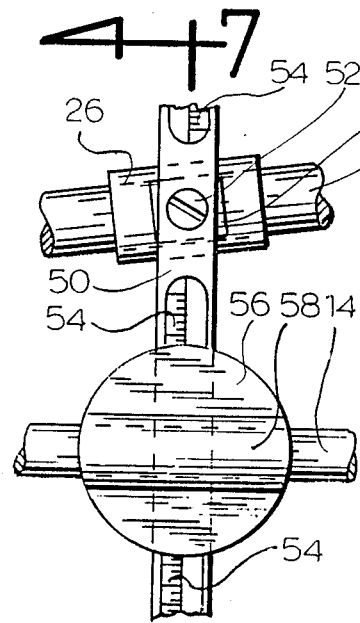
Figure 8:
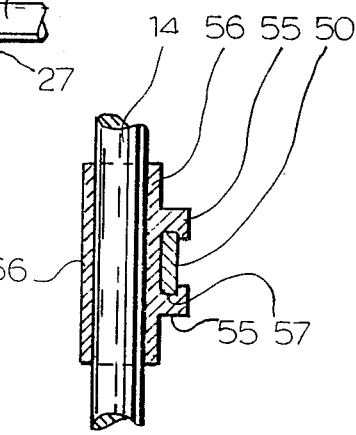
FIG. 8 is a cross-sectional view taken along line 8—8 of FIG. 7.

Ruler 50 has two separate graduated scales 54 and 54a on each side of pivot 52. Two opposite inturned hooks 55 (FIG. 8), dependent from the center of a circular plate 56 (FIG. 6), define therebetween guide tracks 57 slidably engaged by ruler 50. Guide tracks 57 extend parallel to plate 56, radially thereof and through its central axis. To the opposite face of circular plate 56 is integrally mounted a further sleeve 58 slidably and rotatively engaged by arm 14 in between limit positions defined by window 44 and bolt 20. The axes of sleeve 58 and guide tracks 57 are orthogonal to each other.

Hence, ruler 50 is both slidable transversely of arm 14 and lengthwisely thereof (in between limit positions in register with the spirit levels 38, 42) by same displacement of plate 56 and of its sleeve 58, cooperatively with its pivotal mounting to arm 16 at 52. Plate 56 is slidable along ruler 50 to either side of pivot 52 and used to read either scales 54, 54a.

Figure 9:
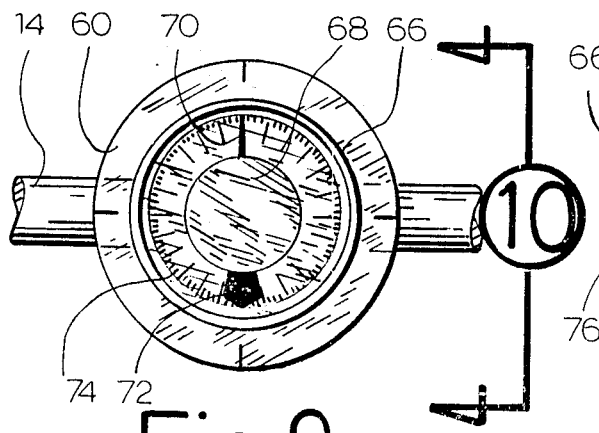
Figure 10:
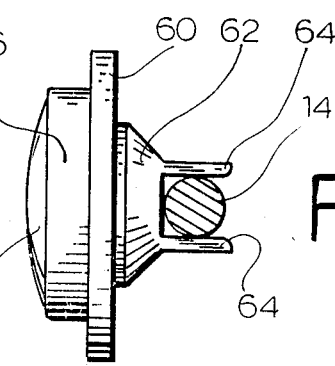
FIG. 10 is a cross-sectional view taken along line 10—10 of FIG. 9.

Another circular plate 60 is mounted to arm 14 through a central yoke member 62 (FIGS. 9-10), defining two resilient legs 64 prebiased one toward the other. The opposite face of plate 60 carries a cylindrical flange 66, into which is axially mounted a freely rotatable needle assembly 68, which carries a radial needle 70 and a diametrically opposite counterweight 72. Plate 60 is positioned intermediate bolt 20 and sleeve 58 and slidable between these two limit positions and also rotatable about arm 14. Plate 60 is rotated to a vertical position, whereby counterweight 72 constantly urges needle indicator 70 in upright, vertical position. A circular, 360-degree directional scale 74, is mounted on plate 60, in register with and behind needle 70. When a glass dome 76 is added to the outer face of wheel 66, one obtains a conventional directional (gravitational) goniometer 60-76.

The relative movement of the constituting elements of the present device 12 can now be readily understood. Each rod 28, 30 may pivot around rod 18 or 24: arrows 78; and lengthwise 14 of same rod: arrows 80. Ruler 50 is slidable transversely of arm 14: arrows 82; pivotable around pivot screw 52 in sleeve 26: arrows 84; slidably carried by the latter sleeve 26 lengthwise 14 of arm 16: arrows 86; and slidably carried by sleeve 58 lengthwise 14 of arm 14: arrows 88. Rod 24 is slidable about sleeve 26 lengthwise 14 of arm 16: arrows 86. Arm 16 and rod 18, 24 are pivotable around bolt 20, relative to arm 14: arrows 90. And goniometer 60-76 is slidable lengthwise of arm 14: arrows 92 and is also rotatable about arm 14.

Arms 14 and 16 and ruler 50 form the three sides of a deformable right triangle with arm 16, being the hypotenuse.

Goniometer 60 can be fitted to either one of arms 14 and 16, and can be used as an alternate in addition to spirit levels 38 or 42.

Figure 2:
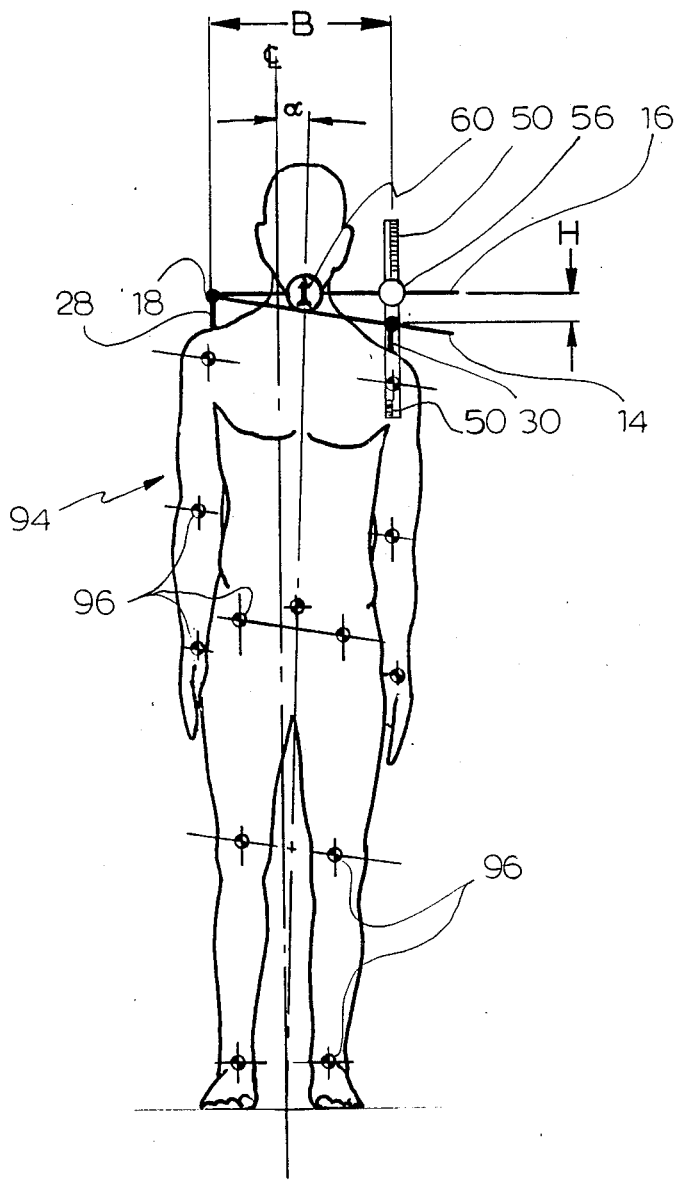
FIG. 2 is a schematic front elevation of a human body, with said measuring device operatively mounted about the shoulders of the human body.

As shown in FIG. 2, the measuring device 12 according to the invention is designed to be used on a human body 94. Device 12 is specifically adapted to measure vertical differences between the axes of skeleton joints 96, and therefore to identify and measure abnormal body posture. Device 12 may be used about the shoulder and neck portion of the person 94, as illustrated, or anywhere else at a skeleton joint of the body, for that matter.

In the manner shown in FIG. 2, for using the device, feeler rods 28, 30 are applied on top of the shoulders and the triangle arrangement angularly deformed until arm 14 becomes horizontal as determined either by goniometer 60-76 or spirit level 42. A reading of scale 54 or of scale 54a at plate 56, depending on which shoulder is lower, will measure the vertical differential of the two shoulders. Scale 48 is used to measure horizontal distances between body parts touched by feeler rods 28 and 30. Since rods 18 and 24 are cylindrical, feeler rods 28 and 30 can be oriented in any direction. Hence the device is highly versatile.

The scalers 48, 50 are to be used cooperatively with comparison charts of "normal" dimensions of body portions and body posture ratios data.

What I claim is:

1. A skeleton-measuring device comprising one and another main arms, said arms being elongated, rigid, and cylindrical; first mounting means interconnecting said arms for pivotal movement of said another arm relative to said one arm about a first plate; support means for supporting said another arm over joint portions of a human body; level means for monitoring horizontal levelling of both of said arms; a scale member connected to said one arm by second mounting means and to said another arm by third mounting means, for both pivotal movement about a second plane parallel to said first plate and lengthwise displacement relative to either of said arms; and scale means for measuring the lengthwise displacement of the scale member relative to said another arm; wherein said support means includes one and another rod member, said one rod member fixedly connected to said another arm, said another rod member connected to said another arm by said third mounting means and adapted for lengthwise displacement relative to said another arm, said rod members orthogonal to said first plane of pivotal movement of said another arm.

2. A device as in claim 1, wherein each of said rod members includes: a rod, which is elongated, rigid and cylindrical; and an abutment member connected to said rod for both lengthwise displacement and pivotal movement thereabout; said abutment member adapted to abut against said joint portions of the human body.

3. A device as in claim 2, wherein each said abutment member includes set-screw means to lock same in releasable fashion against further lengthwise and pivotal movement thereof.

4. A skeleton-measuring device comprising one and another main arms, said arms being elongated, rigid, and cylindrical; first mounting means interconnecting said arms for pivotal movement of said another arm relative to said one arm about a first plane; support means for supporting said another arm over joint portions of a human body; level means for monitoring horizontal levelling of both of said arms; a scale member connected to said one arm by second mounting means and to said another arm by third mounting means, for both pivotal movement about a second plane parallel to said first plane and lengthwise displacement relative to either of said arms; and scale means for measuring the lengthwise displacement of the scale member relative to said another arm; wherein said lengthwise displacement of said scale member along said one arm in one direction is made concurrently with a lengthwise displacement of same scale member along said another arm, but in an opposite direction, relative to said first mounting means.

5. A skeleton-measuring device comprising one and another main arms, said amrs being elongated, rigid, and cylidnrical; first mounting means interconnecting said arms for pivotal movement of said another arm relative to said one arm about a first plane; support means for supporting said another arm over joint portions of a human body; level means for monitoring horizontal levelling of both of said arms; a scale member connected to said one arm by second mounting means and to said another arm by third mounting means, for both pivotal movement about a second plane parallel to said first plane and lengthwise displacement relative to either of said arms; and scale means for measuring the lengthwise displacement of the scale member relative to said another arm; wherein said level means includes one spirit level, embedded in each of said arms at opposite end portions thereof and each visible through a window made in the wall of said arms; said scale member slidable lengthwisely in between two limit positions in register with either one of the spirit levels, respectively.

6. A device as in claim 5, further including a gravitational goniometer means for monitoring vertical levelling of said one arm.

7. A device as in claim 6, wherein said goniometer means includes a rigid casing, mounted to said one arm for lengthwise displacement in between two limit positions defined by said first and second mounting means, respectively.

8. A device as in claim 7, wherein said scale means is a scale plate embedded in said another arm, but which opens through an elongated window made in the wall of said another arm and on the same side as the windows for said spirit levels.

9. A device as in claim 8, wherein said goniometer casing includes a yoke member releasably engageable with and slidable along and rotatable about either one of said arms.

* * * * *